(12) United States Patent
Reichow et al.

(10) Patent No.: US 8,608,313 B2
(45) Date of Patent: Dec. 17, 2013

(54) TRAINING AND/OR MEASURING VISUAL FOCUSING AND VERGENCE ABILITIES USING A PLURALITY OF OPTICAL ELEMENTS

(75) Inventors: Alan W. Reichow, Beaverton, OR (US); Herb Yoo, Beaverton, OR (US)

(73) Assignee: Nike, Inc., Beaverton, OR (US)

( * ) Notice: Subject to any disclaimer, the term of this patent is extended or adjusted under 35 U.S.C. 154(b) by 0 days.

(21) Appl. No.: 13/085,025

(22) Filed: Apr. 12, 2011

(65) Prior Publication Data
US 2012/0265109 A1      Oct. 18, 2012

(51) Int. Cl.
*A61B 3/00* (2006.01)
*A61H 5/00* (2006.01)

(52) U.S. Cl.
CPC ............................. *A61H 5/00* (2013.01)
USPC ............................... 351/203; 351/246

(58) Field of Classification Search
USPC ......... 351/239–240, 222–223, 229–230, 205, 351/218, 200–203
See application file for complete search history.

(56) References Cited

U.S. PATENT DOCUMENTS

| | | | |
|---|---|---|---|
| 1,962,800 A * | 6/1934 | Aspenleiter | 351/229 |
| 3,861,790 A | 1/1975 | Tamura | |
| 5,050,982 A | 9/1991 | Meissner | |
| 5,268,710 A | 12/1993 | Anstey | |
| 5,281,984 A | 1/1994 | Burton | |
| 5,478,239 A | 12/1995 | Fuerst | |
| 5,984,473 A | 11/1999 | Livnat | |
| 6,062,691 A * | 5/2000 | Markson | 351/203 |
| 6,755,525 B2 | 6/2004 | Reichow | |
| 6,811,258 B1 | 11/2004 | Grant | |
| 6,893,127 B2 | 5/2005 | Reichow | |
| 7,073,208 B2 | 7/2006 | Penque | |
| 2004/0012758 A1 | 1/2004 | Lin | |

OTHER PUBLICATIONS

Reichow, et al., "Introduction to Behavioral Optometry", Sports Vision, 1993, 75 pages, Optometric Extension Program Foundation, United States.
Ferreira, "An Overview of Research in Sports Vision: its History and an Optometric Perspective", The South African Optometrist, Dec. 2003, pp. 142-149, vol. 62, No. 4, Auckland Park, South Africa.
Coffey, et al., "Visual Performance Enhancement in Sports Optometry", Sports Vision 1995, pp. 158-177, Butterworth-Heinermann, United States.

(Continued)

*Primary Examiner* — Scott J Sugarman
*Assistant Examiner* — Robert E Tallman
(74) *Attorney, Agent, or Firm* — Shook, Hardy & Bacon L.L.P.

(57) ABSTRACT

The visual focusing and/or vergence abilities of a subject may be trained and/or tested using apparatuses and methods in accordance with the present invention. The subject may be provided with an apparatus having optical elements having different optical characteristics and instructed to look through an optical element having a first optical characteristic and to focus on an indicia or object. The subject may be instructed to rotate the apparatus and to look through optical elements having a second optical characteristic and to focus on the same or different indicia or object. The subject may be instructed to repeat this process with this or further apparatuses having optical elements having the same or different optical characteristics. The visual focusing and/or vergence abilities of a subject may thus be tested and/or trained.

33 Claims, 6 Drawing Sheets

(56) References Cited

OTHER PUBLICATIONS

Cardall, "Contact Lenses in Sport: a General Overview", Optician, Jan. 13, 2006, pp. 22-25, vol. 231, No. 6034, United States.

Rouse, et al., "A Comparison Study of Dynamic Visual Acuity Between Athletes and Nonathletes", Journal of the American Optometric Association, Dec. 1988, pp. 946-950, vol. 59, No. 12, United States.

Koenig, "Practicing Perception: Eyes Can Be Trained to be More Effective", USA Today Baseball Weekly, 1996, 3 pages, United States.

Coffey, et al., "Optometric Evaluation of the Elite Athlete," Problems in Optometry, Mar. 1990, pp. 32-59, vol. 2, No. 1, United States.

Reichow, et al., "A Comparison of Contrast Sensitivity in Elite Athletes Versus a Normal Population", American Journal of Optometry and Physiological Optics, Dec. 15, 1986, vol. 63, No. 82, United States.

Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.

Herdman, et al., "Computerized Dynamic Visual Acuity Test in the Assessment of Vestibular Deficits", The American Journal of Otology, 1998, pp. 790-796, vol. 19, No. 6, United States.

Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.

International Search Report and Written Opinion of Jul. 23, 2012 for PCT/US2012/033044.

\* cited by examiner

TRAINING AND/OR MEASURING VISUAL FOCUSING AND VERGENCE ABILITIES USING A PLURALITY OF OPTICAL ELEMENTS

CROSS-REFERENCE TO RELATED APPLICATIONS

Not applicable.

STATEMENT REGARDING FEDERALLY SPONSORED RESEARCH OR DEVELOPMENT

Not applicable.

TECHNICAL FIELD

The present invention relates to systems and methods for training the visual abilities of individuals. More particularly, the present invention relates generally to training and/or measuring the visual focusing and vergence abilities of a subject.

BACKGROUND OF THE INVENTION

The ability to focus clearly and accurately on a point at a specific location relative to an individual is an important feature of human vision. Moreover, the ability to quickly focus on an object or visual indicia at a given distance from an individual, or to quickly shift visual focus from a first distance to a second distance, may be advantageous in a number of human endeavors. For example, a person who can quickly focus on one object and then change focus to another object may possess certain advantages over a person who can not change focus as quickly.

Both focusing and verging ability may be necessary to provide these advantages. For instance, a person may possess acceptable focusing abilities but lack acceptable vergence abilities. This may cause the appearance of two objects because the eyes have not verged sufficiently (although the objects will appear clearly focused). This may cause problems for the person in quickly and accurately detecting or following a fast-moving object, for example. Or, in an alternative example, a person may be able to verge his or her eyes on an object very quickly, but may not be able to quickly focus the eyes on the object. The object may thus appear blurry, although there will appear to be only one object as the person's eyes have verged on the object. This may cause difficulties in accurately distinguishing one object from another, for example. It may thus be advantageous to be able to measure and/or train a person's focusing and vergence abilities either separately or together. However, separately testing and/or improving focusing and vergence ability is a challenge because both skills are typically utilized together in visual tasks.

Superior visual focusing and vergence ability may prove advantageous, for instance, in various sports, athletics, leisure activities, or any number of human endeavors because a person who can focus and verge more quickly may be able to react more quickly or accurately to a visual stimulus or multiple visual stimuli. The ability to quickly shift visual focus and/or vergence may also be beneficial for a number of activities, such as driving. Given that visual focusing and vergence ability can be advantageous in various human endeavors, it can be beneficial to efficiently and accurately measure the visual focusing and vergence abilities of a subject to identify weaknesses in a subject's visual focusing and vergence abilities. Further, an individual may wish to improve his or her visual focusing and/or vergence capabilities, either to improve upon a weakness or to further enhance an ability.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

The present invention relates to training and/or measuring the visual abilities of a subject. More particularly, the present invention provides apparatuses and methods that may be utilized to improve the visual focusing and/or vergence capabilities of a subject. Apparatuses in accordance with the present invention may include two or more optical elements, each optical element possessing a different optical characteristic, for example. Methods in accordance with the present invention may include instructing a subject to look at an indicia through a first optical element. The subject may then be asked to look at the indicia through the second optical element. The time it takes a subject to perform this task may be measured. The visual ability of a subject may thus be measured. Further, the subject may be asked to repeatedly perform the method.

In a more specific example, the optical elements may include lenses with the optical characteristics of, for example, focal length. In this example, when looking through the first lens, the first lens having as a first optical characteristic a first focal length, the subject must focus his or her eyes on an indicia. The subject may then be asked to look through a second lens, the second lens having as a second optical characteristic a second focal length. The subject will again be asked to focus on the indicia. The time required for the subject to accurately perform this task may be measured to assess the focusing ability of the subject. Alternatively, the subject may be asked to repeatedly perform the task until he or she improves his or her focusing abilities.

In another example, the optical elements may include prisms with the optical characteristics of, for example, prism angle. In this example, when looking through the first prism, the first prism having as an optical characteristic a first prism angle, the subject must verge his or her eyes to see a displayed indicia. The subject may then be asked to look through a second prism, the second prism having as a second optical characteristic a second prism angle. The subject will again be asked to verge his or her eyes to see the displayed indicia. Similarly to the above example, the time required for the subject to perform this task may be measured to assess the vergence ability of the subject. Alternatively, the subject may be asked to repeatedly perform the task until he or she improves his or her vergence abilities. It can thus be appreciated how the vergence and focusing abilities of a subject may be separately measured and/or trained.

In another example in accordance with the present invention, a subject may be provided with a first apparatus comprising a plurality of lenses of different focal lengths. The subject may be instructed to utilize this first apparatus to first visually focus on an indicia while looking through a first lens of a first focal length, and then to visually focuses on an indicia while looking through a second lens of a second focal length, the first and second lenses having a first lens strength difference between them. By utilizing the first apparatus to repeatedly switch between focusing on indicia while through the first and second lenses, the subject may improve his or her focusing abilities.

After the subject has performed adequately at focusing while switching between looking through the first and second lenses having the first lens strength difference, the subject may be provided with a second apparatus comprising lenses having a second lens strength difference, the second lens strength difference exceeding the first lens strength difference. These lenses may also differ specifically in focal length, giving them a second lens strength difference, the second lens strength difference perhaps being greater than the first lens strength difference. The subject may then be asked to switch between the lenses on the second apparatus and focus on indicia until his or her performance improves to a desired level. This process may be repeated any number of times utilizing a number of different apparatuses, each comprising a number of lenses having a number of lens strength differences. By having the subject focus on indicia while looking through different lenses having certain lens strength differences, the subject's visual focusing abilities may be improved. It should be noted that it may be advantageous to progressively increase the lens strength differences of the lenses that the subject must switch between and focus through, although any order of lens strength differences may be utilized to train a subject.

A further example in accordance with the present invention provides apparatuses and methods that can be utilized to improve and/or measure the visual vergence capabilities of a subject. A subject may, for example, be provided with a first apparatus comprising a plurality of prisms possessing different characteristics, such as different prism angles. The subject may be instructed to utilize this first apparatus to first visually focus on an indicia while looking through a first prism having a first prism angle, and then to visually focuses on an indicia while looking through a second prism having a second prism angle, the first and second prisms having a first angle difference between them. By utilizing the first apparatus to repeatedly switch between focusing on indicia while through the first and second prisms, the subject may improve or measure his or her vergence abilities.

Similarly to the process described above for utilizing lenses to train the focusing ability of a subject, after the subject has performed adequately at focusing while switching between looking through the first and second prisms having the first prism angle difference, the subject may be provided with a second apparatus comprising prisms having a second prism angle difference, the second prism angle difference exceeding the first prism angle difference. These prisms may also differ specifically in prism angle, giving them a second prism angle difference, the second angle difference perhaps being greater than the first angle difference. The subject may then be asked to switch between the prisms on the second apparatus and focus on indicia until his or her vergence performance proves adequate. This process may be repeated any number of times utilizing a number of different apparatuses, each comprising a number of prisms having a number of prism angle differences. By having the subject focus on indicia while looking through different prisms having certain prism angle differences, the subject's visual vergence abilities may be improved. It should be noted that it may be advantageous to progressively increase the prism angle differences of the prisms that the subject must switch between and focus through, although any order of prism angle differences may be utilized to train a subject as would be obvious to one of ordinary skill in the art.

Another aspect of the present inventions provides apparatuses and methods that can be utilized to measure the performance of a subject who first visually focuses on an indicia when looking through a first lens of a first focal length, and who then visually focuses on an indicia when looking through a second lens of a second focal length. In this way, the subject's visual focusing abilities may be measured objectively. Similarly, an aspect of the present inventions also provides apparatuses and methods that can be utilized to measure the performance of a subject who first visually focuses on an indicia when looking through a first prism having a first angle, and who then visually focuses on an indicia when looking through a second prism having a second angle. In this way, the subject's visual vergence abilities may be measured objectively. Methods and apparatuses in accordance with the present invention may be used to quickly and accurately measure the focusing and/or vergence abilities of a subject, to identify weaknesses in a subject's focusing and/or vergence abilities, and to train subjects in their visual focusing and/or vergence capabilities.

DETAILED DESCRIPTION OF THE INVENTION

The subject matter of the present invention is described with specificity herein to meet statutory requirements. However, the description itself is not intended to limit the scope of this patent. Rather, the inventors have contemplated that the claimed subject matter might also be embodied in other ways, to include different components, steps, or combinations of components or steps similar to the ones described in this document, in conjunction with other present or future technologies.

Methods and apparatuses in accordance with the present invention may be used to measure the visual focusing abilities of a subject. In accordance with the present invention, an apparatus may include a frame, a plurality of coplanar optical elements having optical characteristics, and a handle, the handle not being coplanar to the optical elements. The optical elements may include, for example, coplanar lenses having varying focal lengths. In another example in accordance with the present invention, an apparatus may include a frame, a plurality of coplanar prisms having varying prism angles, and a handle not being coplanar to the prisms of varying prism angles.

Also in accordance with the present invention, an apparatus may include a partially cylindrical frame, a plurality of optical elements oriented generally along the circumferential surface of the partially cylindrical frame, and a handle oriented generally along the axis of the partially cylindrical frame.

Further in a method in accordance with the present invention, a subject may be instructed to hold the apparatus by the handle such that a first lens of a first focal length may be visually aligned with the subject's eyes, to look through the first lens and focus on an indicia, to rotate the apparatus about the handle so that a second lens of a second focal length may be visually aligned with the subject's eyes, and to look through the second lens and focus on an indicia.

In yet another method in accordance with the present invention, a subject may be instructed to hold the apparatus by the handle such that a first prism having a first prism angle may be visually aligned with the subject's eyes, to look through the first prism and focus on an indicia, to rotate the apparatus about the handle so that a second prism of a second prism angle may be visually aligned with the subject's eyes, and to look through the second prism and focus on an indicia.

By utilizing methods and apparatuses in accordance with the present invention, the visual focusing and/or vergence abilities of a subject can be trained or may be efficiently and accurately measured.

Figure 1A:
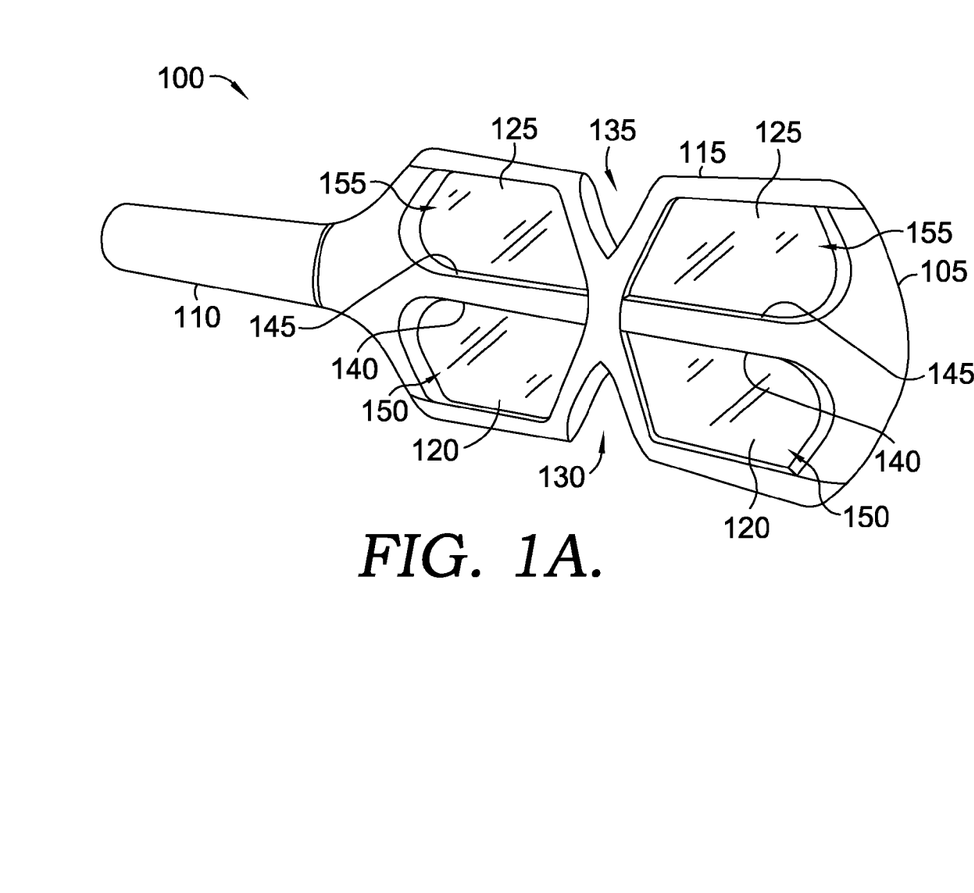
FIG. 1A illustrates a perspective view of an apparatus in accordance with the present invention.

Referring now to FIG. 1A, a perspective view of an apparatus 100 in accordance with the present invention is illustrated. In this example, the apparatus 100 comprises a frame 105, a first pair of openings to receive optical elements 150, a second pair of openings to receive optical elements 155, a first pair of optical elements 120, a second pair of optical elements 125, a first nose notch 130, a second nose notch 135, a first edge 140, a second edge 145, and a handle 110.

Figure 1B:
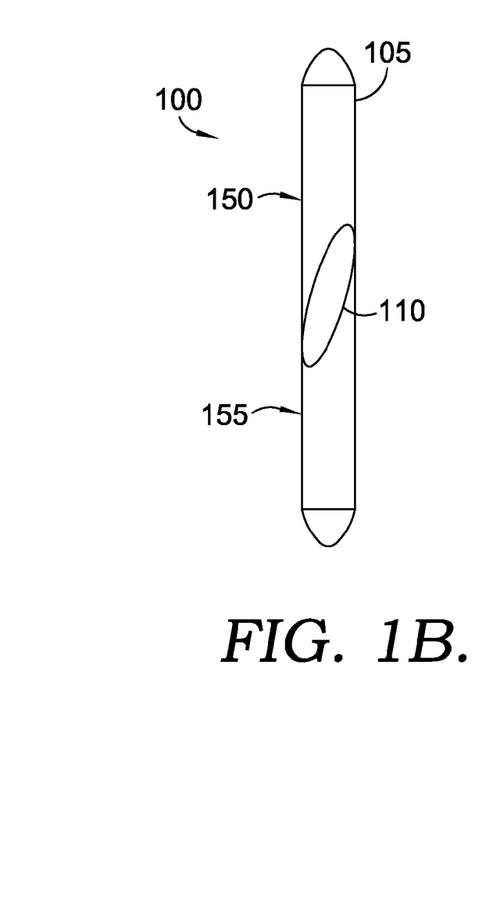
FIG. 1B illustrates a side view of an apparatus in accordance with the present invention.

FIG. 1B depicts a side view of the apparatus 100 in accordance with the present invention. From this side view it can be observed that, in this example, the frame 105 is coplanar with the first pair of openings 150, the second pair of openings 155, the first pair of optical elements 120, and the second pair of optical elements 125. It may also be observed from this side view that the handle 110 is not coplanar to the frame 105, the first pair of openings 150, the second pair of openings 155, the first pair of optical elements 120, and the second pair of optical elements 125. That the handle 110 is not coplanar to these components provides for advantageous rotation of the apparatus 100. It should be noted that the first pair of optical elements 120 and the second pair of optical elements 125 may include lenses, prisms, or other optical elements possessing optical characteristics that may be used to measure and/or train the visual focusing and/or vergence abilities of a subject. The handle 110, first nose notch 130, and second nose notch 135 may be composed of a material to provide for increased comfort for the user of the apparatus 100. It should also be noted that the use of overmolds on certain components can increase the appearance of refinement of the apparatus 100. One of ordinary skill in the art will appreciate that these components or any components of the apparatus may be composed of or covered by a material that could provide increased comfort and appearance of refinement to the user of the apparatus 100.

Figures 2A, 2B, 2C:
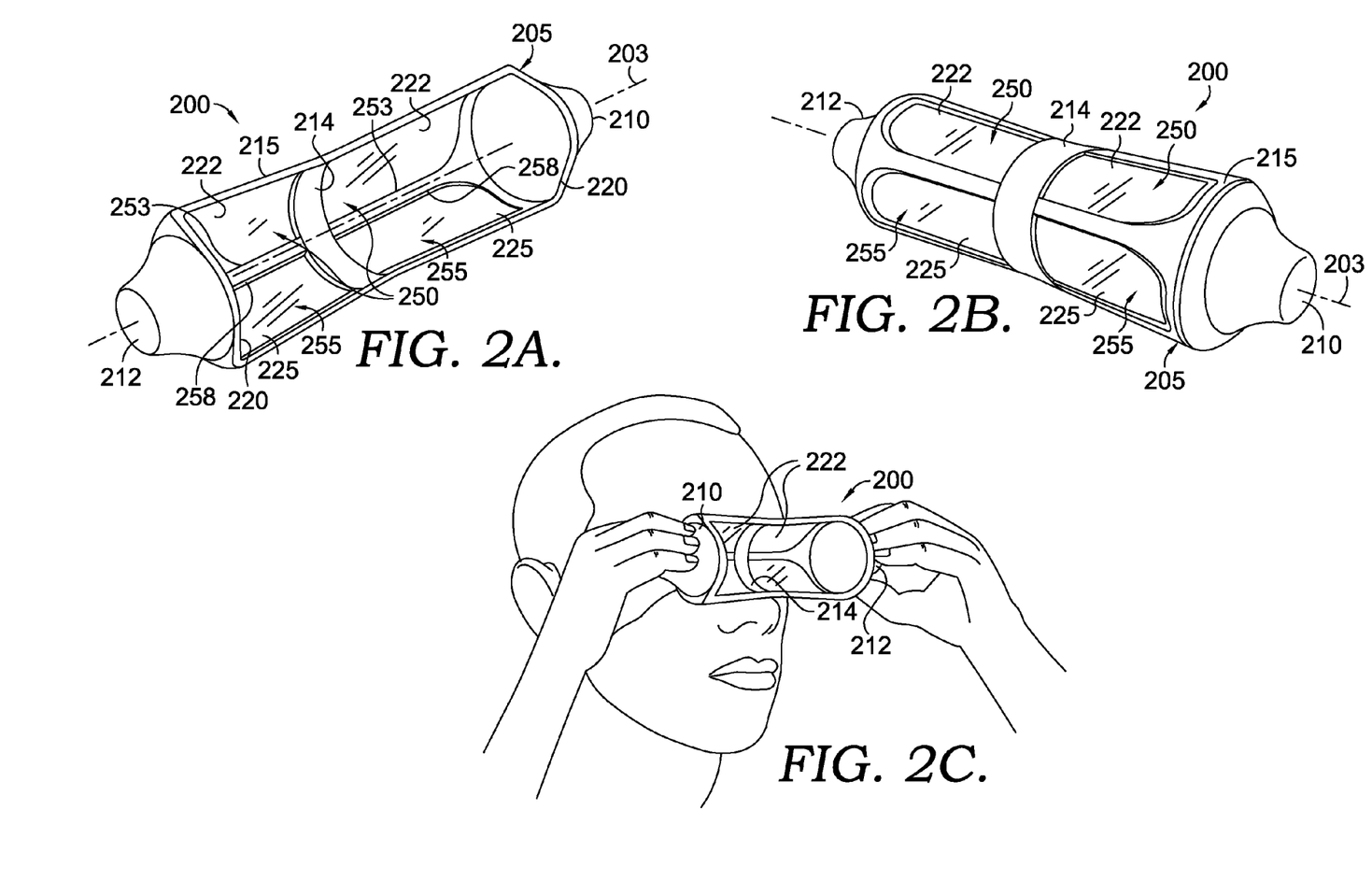
FIG. 2A illustrates a rear perspective view of a further apparatus in accordance with the present invention.
FIG. 2B illustrates a front perspective view of a further apparatus in accordance with the present invention.
FIG. 2C illustrates a rear perspective view of a further apparatus in accordance with the present invention in use by a subject.

Referring now to FIG. 2A, a rear perspective view of a further apparatus 200 in accordance with the present invention is illustrated. In this example, the apparatus 200 comprises a partially cylindrical frame 205, a circumferential surface 215, a pair of axial boundaries 220, a first pair of openings to receive optical elements 250, a first pair of axially oriented edges 253, a second pair of openings to receive optical elements 255, a second pair of axially oriented edges 258, a first pair of optical elements 222, a second pair of optical elements 225, a fixed handle 210, a pivoting handle 212, and a bridge 214.

FIG. 2B depicts a front perspective view of the apparatus 200 in accordance with the present invention. From this side view it can be observed that, in this example, the bridge 214, fixed handle 210, and pivoting handle 212 may be composed of a material that may provide increased comfort to a user of the apparatus 200. It should also be noted that the use of overmolds on certain components can increase the appearance of refinement of the apparatus 200. Many components of the apparatus 200 may be composed of or covered by a material that could provide increased comfort and the appearance of refinement to the user of the apparatus 200.

It may also be observed from this front perspective view that the fixed handle 210 and the pivoting handle 212 are generally oriented along the axis 203 of the partially cylindrical frame 205. It may be further observed that the first pair of openings 250, the second pair of openings 255, the first pair of optical elements 222, and the second pair of optical elements 225 is oriented generally along the circumferential surface 215.

It should be noted that by orienting various components generally along the circumferential surface 215 of the partially cylindrical frame 205, and the fixed handle 210 and the pivoting handle 212 along the axis 203 of the partially cylindrical frame 205, the pairs of optical elements may be easily rotated about the axis 203 of the partially cylindrical frame 205 by use of the fixed handle 210 and the pivoting handle 212. It should further be noted that the apparatus 200 may allow for easier rotation of the partially cylindrical frame by allowing a user to rotate the fixed handle 210 with one hand and hold the pivoting handle 212 with another hand. Alternatively, apparatus 200 could include two fixed handles, two pivoting handles, or any combination of pivoting and fixed handles to further supplement the rotational capabilities of apparatuses in accordance with the present invention. It should also be noted that the pivoting handle may be notched such that it may snap into place when rotated by certain amounts, thus allowing for more accurate alignment of the optical elements. For example, a subject may be looking through the first pair of optical elements 222 and begin rotating the apparatus using the pivoting handle 212. When the second pair of optical elements 225 becomes aligned with the subject's eyes, the pivoting handle 212 may "snap" into place such that the subject may more easily halt the rotation while the second pair of optical elements 225 is aligned with the subject's eyes. It should additionally be noted that having the optical elements oriented generally about a partially cylindrical frame and rotating components about the axis advantageously allows for a reduction in the amount of rotation that would be necessary to align an optical element with the subject's eyes were the axis coplanar to the optical elements.

FIG. 2C illustrates a rear perspective view of the apparatus 200 in use by a subject. The subject is seen holding the apparatus 200 by the fixed handle 210 and by the pivoting handle 212. The subject is looking through the first pair of optical elements 222 with the bridge 214 oriented adjacent to the subject's nose.

Figures 3A, 3B, 3C:
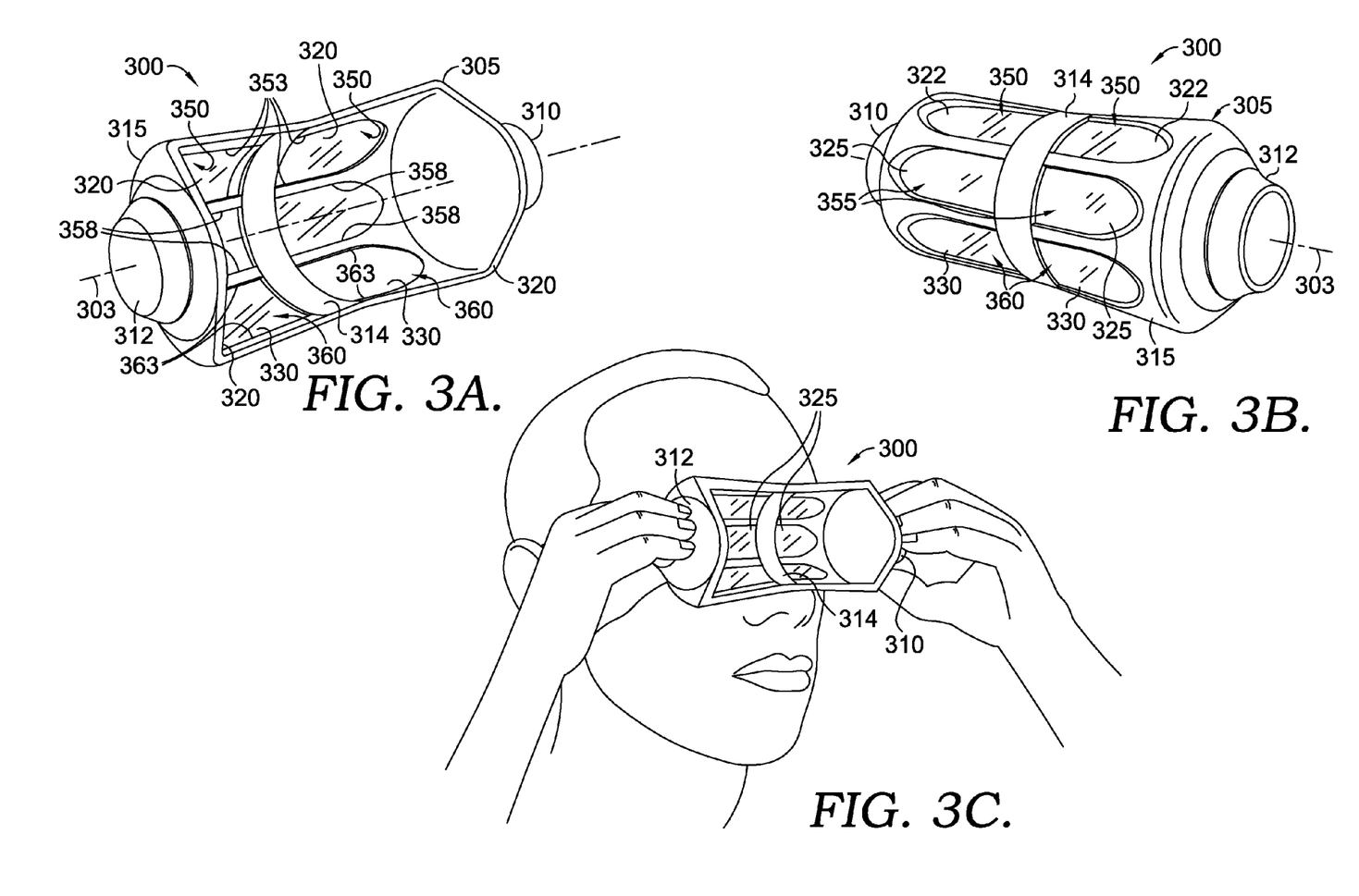
FIG. 3A illustrates a rear perspective view of a further apparatus in accordance with the present invention.
FIG. 3B illustrates a front perspective view of a further apparatus in accordance with the present invention.
FIG. 3C illustrates a rear perspective view of a further apparatus in accordance with the present invention in use by a subject.

Referring now to FIG. 3A, a rear perspective view of a further apparatus 300 in accordance with the present invention is illustrated. In this example, the apparatus 300 comprises a partially cylindrical frame 305, a circumferential surface 315, a pair of axial boundaries 320, a first pair of openings to receive optical elements 350 having a first pair of axially oriented edges 353, a second pair of openings to receive optical elements 355 having a second pair of axially oriented edges 358, a third pair of openings to receive optical elements 360 having a third pair of axially oriented edges 363, a first pair of optical elements 322, a second pair of optical elements 325, a third pair of optical elements 330, a fixed handle 310, a pivoting handle 312, and a bridge 314.

FIG. 3B depicts a front perspective view of the apparatus 300 in accordance with the present invention. From this side view it can be observed that, in this example, the bridge 314, fixed handle 310, and pivoting handle 312 may be composed of a material that may provide increased comfort to a user of the apparatus 300. Components of the apparatus 300 may be composed of or covered by a material that could provide increased comfort to the user of the apparatus 300. It should also be noted that the use of overmolds on certain components can increase the appearance of refinement of the apparatus 300. It may also be observed from this front perspective view that the fixed handle 310 and pivoting handle 312 are generally oriented along the axis 303 of the partially cylindrical frame 305. It may be further observed that the first pair of openings 350, the second pair of openings 355, the third pair of openings 360, the first pair of optical elements 322, the second pair of optical elements 325, and the third pair of optical elements 330 are oriented generally along the circumferential surface 315.

It should be noted that by orienting various components generally along the circumferential surface 315 of the partially cylindrical frame 305, and the fixed handle 310 and the pivoting handle 312 along the axis 303 of the partially cylindrical frame 305, the pairs of optical elements may be easily rotated about the axis 303 of the partially cylindrical frame 305 by use of the fixed handle 312 and the pivoting handle 314. It should further be noted that the apparatus 300 may allow for easier rotation of the partially cylindrical frame 305 by allowing a user to rotate the fixed handle 310 with one hand and hold the pivoting handle 312 with another hand. Alternatively, apparatus 300 could include two fixed handles, two pivoting handles, or any combination of pivoting and fixed handles to further supplement the rotational capabilities of apparatuses in accordance with the present invention. Optical elements could include lenses, prisms, other optical elements possessing different optical characteristics, and combinations thereof. It should also be noted that the pivoting handle may be notched such that it may snap into place when rotated by certain amounts, thus allowing for more accurate alignment of the optical elements. For example, a subject may be looking through the first pair of optical elements 322 and begin rotating the apparatus using the pivoting handle 312. When the second pair of optical elements 325 becomes aligned with the subject's eyes, the pivoting handle 312 may "snap" into place such that the subject may more easily halt the rotation while the second pair of optical elements 325 is aligned with the subject's eyes. After looking through the second pair of optical elements 325, the subject may again rotate the apparatus using the pivoting handle 312 until the device again "snaps" into place, this time aligning the subject's eyes with the third pair of optical elements 330. Any combination of notches in any number of rotational configurations may be thus utilized to allow an apparatus to advantageously "snap" into place while being rotated by the subject. It should additionally be noted that having the optical elements oriented generally about a partially cylindrical frame and rotating components about the axis advantageously allows for a reduction in the amount of rotation that would be necessary to align an optical element with the subject's eyes were the axis coplanar to the optical elements.

FIG. 3C illustrates a rear perspective view of the apparatus 300 in use by a subject. The subject is seen holding the apparatus 300 by the fixed handle 310 and by the pivoting handle 312. The subject is looking through the second pair of optical elements 325 with the bridge 314 oriented adjacent to the subject's nose.

Figure 4:
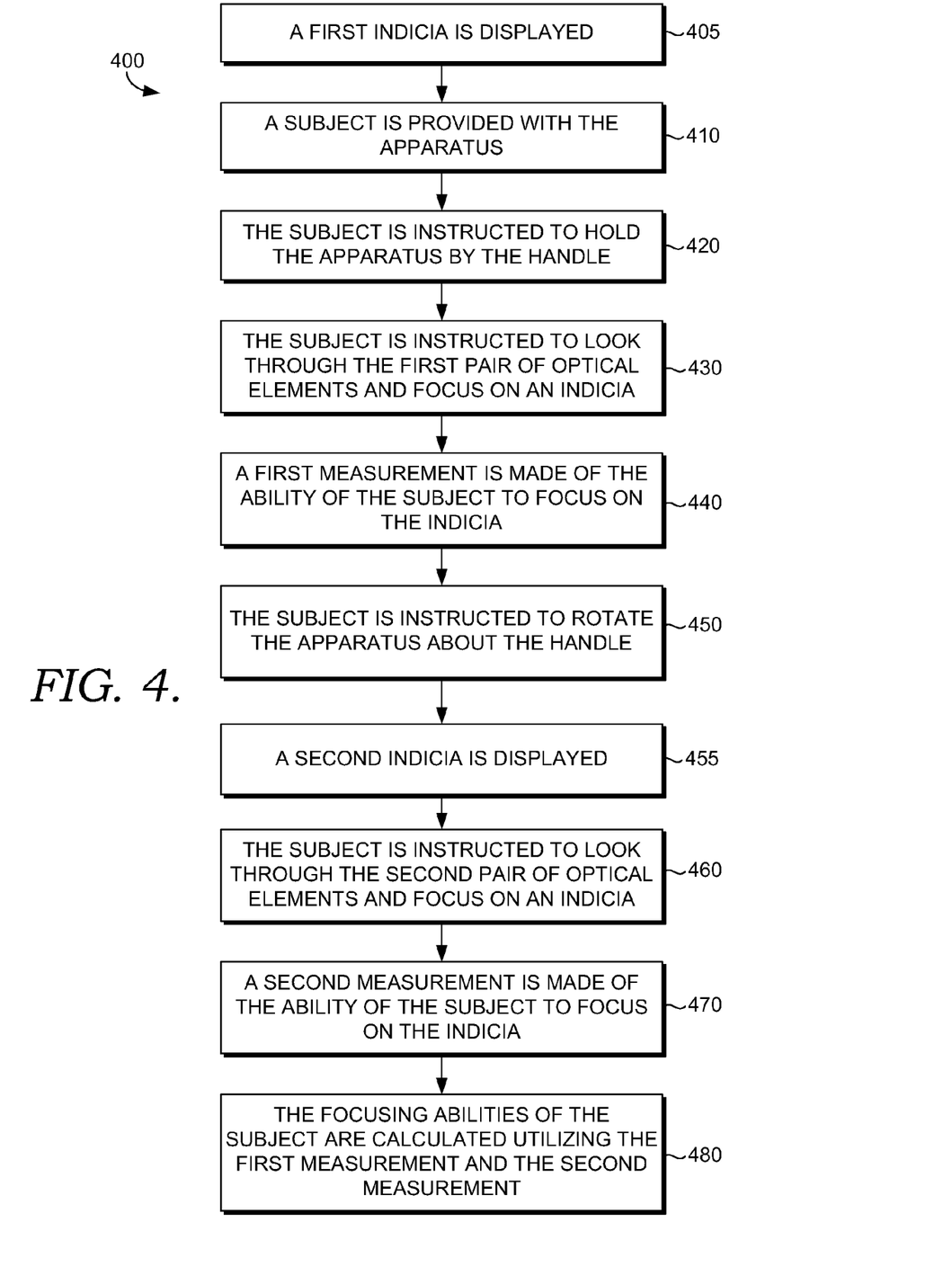
FIG. 4 illustrates a method in accordance with the present invention.

Referring now to FIG. 4, a method 400 in accordance with the present invention is illustrated. Method 400 may be used to train and/or measure the visual focusing and/or vergence abilities of a subject. Of course, the steps of method 400 may be performed in orders different than those described herein and illustrated in FIG. 4, and the steps of method 400 may be repeated varying numbers of times or even omitted. In step 405, an indicia is displayed. In step 410, a subject is provided with the apparatus, such as apparatus 100. In step 420, the subject is instructed to hold the apparatus, such as apparatus 100 by the handle 110. In step 430, the subject is instructed to look through the first pair of optical elements and focus on an indicia. In step 440, a first measurement is made of the ability of the subject to focus on the indicia. For example, the accuracy and/or speed with which a subject perceived indicia may be recorded. In step 450, the subject is instructed to rotate the apparatus about the handle. In step 455, a second indicia is optionally displayed. In step 460, the subject is instructed to look through the second pair of optical elements and focus on an indicia. In step 470, a second measurement is made of the ability of the subject to focus on the indicia. For example, the accuracy and/or speed with which a subject perceived indicia may be recorded. In step 480, the focusing abilities of the subject can be calculated utilizing the first measurement and the second measurement.

It should be noted that method 400 may be adapted to train and/or measure the visual focusing and/or vergence abilities of a subject. If method 400 were to be used solely for training visual focusing ability, for example, step 440 and step 470, wherein measurements are made of a subject's focusing abilities, might be omitted from method 400. Similarly, step 480, wherein the focusing abilities of the subject can be calculated utilizing the first measurement and the second measurement, may also be advantageously omitted were the method illustrated in FIG. 4 being used to train a subject, rather than to measure the subject's focusing abilities. It should be noted that the measurements made may include the measuring the rate of accuracy over time to assess the visual focusing and/or vergence abilities of a subject over different periods of time. For example, a subject may be adept at visually focusing on an indicia in a first training session, being both accurate and quick at detecting the indicia. Over the course of subsequent tests, however, the subject's accuracy and/or speed may decline, perhaps due to fatigue. For instance, a subject may be asked to repeatedly perform the method illustrated in FIG. 4. The subject may perform the method five times, and, for example, the time it takes the subject to perform the method may be 30 seconds, 31 seconds, 33 seconds, 38 seconds, and 45 seconds, respectively. These time measurements may demonstrate that the subject may be experiencing increasing difficulty as the method is repeatedly performed. This may indicate, for instance, that the subject's endurance may be advantageously trained to reduce the fatigue the subject may experience. By measuring the rate of accuracy and/or speed over time, fatigue or other characteristics may be measured and/or trained. Training may increase the subject's abilities to perform tasks that require visual endurance. For example, a subject may have difficulty in making free throws at the end of basketball games. The cause of this difficulty may be that the subject is experiencing vision fatigue at the end of games. If assessments indicate that the subject suffers from visual fatigue, the subject's endurance may be trained by methods in accordance with the present invention. This may in turn increase the subject's free throw performance at the end of games.

In another example of training a subject in accordance with an embodiment in accordance with the present invention, by first focusing on an indicia while looking through a first pair of lenses and then focusing on an indicia while looking through a second pair of lenses, the first and second pair of lenses having a certain lens strength difference between them, the focusing capabilities of a subject may be trained. Eventually the subject may obtain proficiency at switching between these two pair of lenses with a certain lens strength difference, at which point the subject may be instructed to utilize a training using two different pair of lenses having a greater lens strength difference. The above illustrated methods may be advantageously repeated any number of times and in any order, with pairs lenses or prisms of varying lens strength differences or angle differences, respectively, as the visual focusing and/or vergence abilities of an individual improve.

Figure 5:
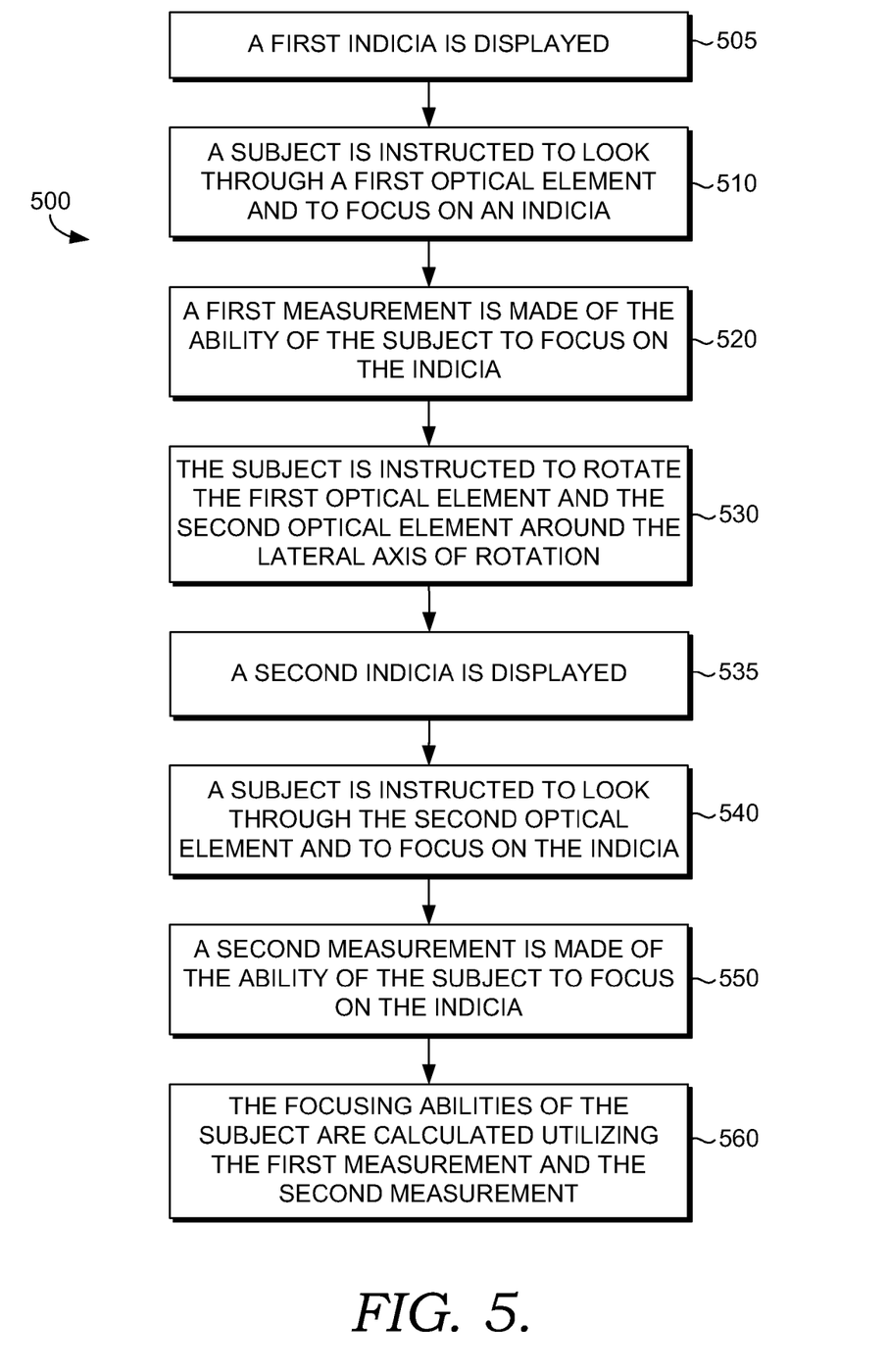
FIG. 5 illustrates a further method in accordance with the present invention.

Referring now to FIG. 5, a method 500 in accordance with the present invention is illustrated. Method 500 may be used to train and/or measure the visual focusing abilities of a subject. Method 500 may utilize, for example, the various exemplary apparatuses described herein. Of course, the steps of method 500 may be performed in orders different than those described herein and illustrated in FIG. 5, and steps of method 500 may be repeated varying numbers of times or even omitted. In step 505, an indicia is displayed. In step 510, a subject is instructed to look through a first optical element and to focus on an indicia. In step 520, a first measurement is made of the ability of the subject to focus on the indicia. For example, the accuracy and/or speed with which a subject perceived indicia may be recorded. In step 530, the subject is instructed to rotate the first optical element and the second optical element around the lateral axis of rotation. In step 535, a second indicia is optionally displayed. In step 540, a subject is instructed to look through a second optical element and to focus on the indicia. In step 550, a second measurement is made of the ability of the subject to focus on the indicia. For example, the accuracy and/or speed with which a subject perceived indicia may be recorded. In step 560, the focusing abilities of the subject are calculated utilizing the first measurement and the second measurement.

It should be noted that method 500 may be iteratively repeated in order to assess the ability of a subject at performing the different tasks over time. For example, a subject may perform the method a number of times, and each time a measurement of the accuracy and/or speed with which the subject performed could be taken. Over time, a subject's speed and/or accuracy in focusing on an indicia may decline. This may indicate, for example, that the subject is experiencing fatigue in his or her visual focusing abilities. It should be noted that the measurements made may include the measuring the rate of accuracy over time to assess the visual focusing and/or vergence abilities of a subject over different periods of time. For instance, a subject may be asked to repeatedly perform the method illustrated in FIG. 4 ten times. The subject's time to perform the method may be 20 seconds for each of the first eight tests, 25 seconds for the ninth test, and 33 seconds for the tenth test. These time measurements may demonstrate that the subject may be experiencing increasing difficulty performing the visual tasks after eight repetitions. This may indicate that the subject's endurance may be advantageously trained to reduce the fatigue the subject may experience. This may in turn increase the subject's abilities to perform tasks that require visual endurance. Thus, by measuring the rate of accuracy and/or speed over time, fatigue or other characteristics may be measured and/or trained. The subject may in response be trained using methods in accordance with the present invention to improve his or her stamina in performing such visual tasks.

It should also be noted that method 500 may be adapted to train and/or measure the visual focusing abilities of a subject. If method 500 were to be used solely for training visual focusing abilities, for example, step 520 and step 550, wherein measurements are made of a subject's focusing abilities, might be omitted from method 500. Similarly, step 560, wherein the focusing abilities of the subject can be calculated utilizing the first measurement and the second measurement, may also be advantageously omitted were the method illustrated in FIG. 5 being used to train a subject, rather than to measure the subject's focusing abilities. So, for example, by first focusing on an indicia while looking through a first lens and then focusing on an indicia while looking through a second lens, the first and second lenses having a certain lens strength difference, the focusing capabilities of a subject may be improved. Eventually the subject may obtain proficiency at switching between these two lenses, at which point the subject may be instructed to utilize a training method using two different lenses having a greater lens strength difference. The above illustrated methods may be advantageously repeated any number of times and in any order, with lenses of varying lens strength differences, as the visual focusing abilities of a subject improve.

Figure 6:
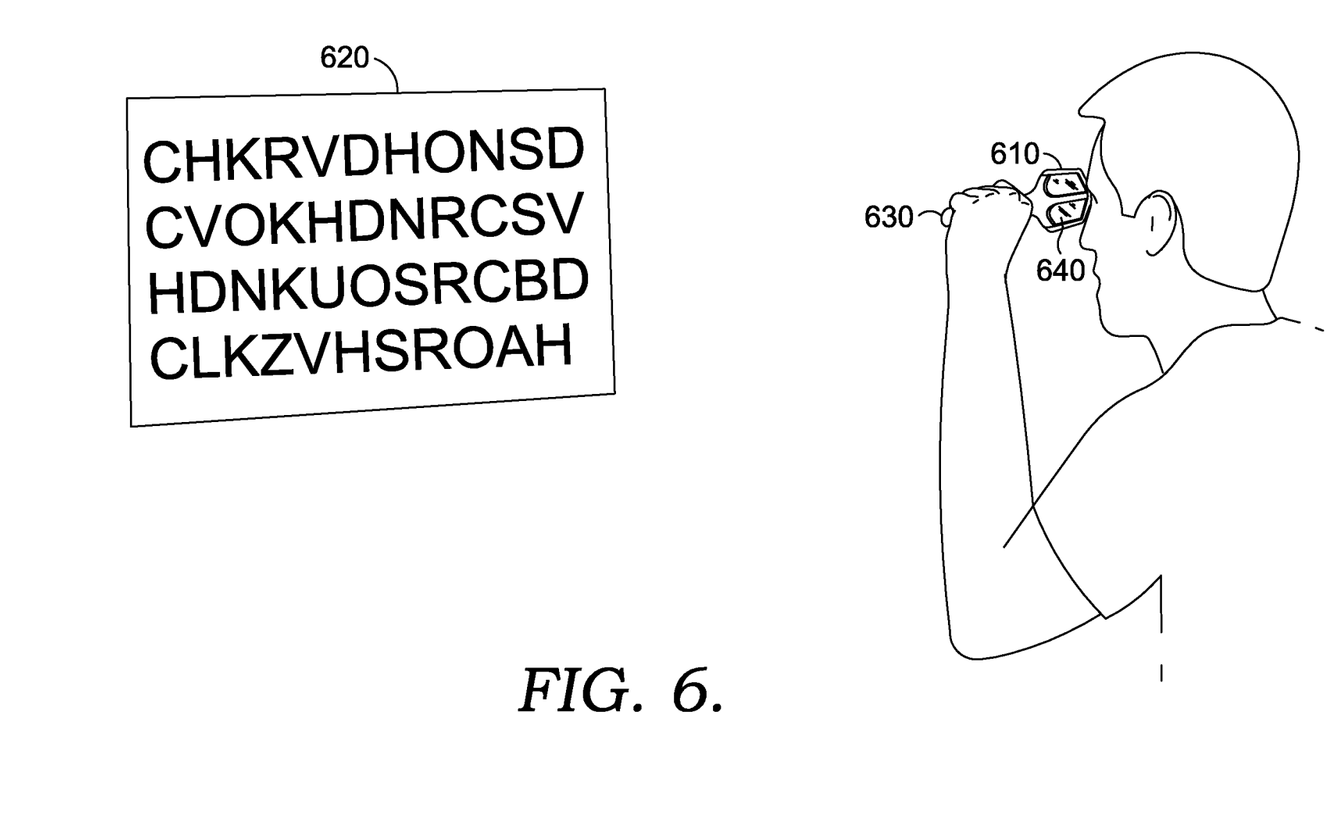
FIG. 6 illustrates an apparatus in accordance with the present invention in use.

FIG. 6 illustrates a subject looking through an apparatus 610 in accordance the present invention at an indicia, in this case an eye chart 620. The subject can be seen holding the apparatus 610 by the handle 630 and looking through a first optical element 640. It should be noted that the chart may be located at varying distances, and may be kept stationary or moved in between tests. This and other configurations would be appreciated by one of ordinary skill in the art.

It should further be noted that while any combination of optical elements having any optical characteristic differences may be utilized to train and/or measure the focusing and/or vergence abilities of a subject, it may be advantageous to use optical elements having certain optical characteristic differences. For example, an apparatus may comprise a lens. A commonly used measure of lens strength is dioptric power, which is typically approximately equal to the reciprocal of the focal length of the lens. An apparatus may advantageously comprise, for example, a first lens of dioptric power +2 and a second lens of dioptric power −2. By utilizing such an apparatus and looking through the first lens and focusing on an indicia, and then looking through the second lens and focusing on an indicia, a subject's focusing capabilities may be efficiently trained. The subject may then be provided with a second apparatus which may comprise, for example, a first lens of dioptric power +2.5, and a second lens of dioptric power −2.5. In another example, the subject may then be provided with a second apparatus which may comprise, for example, a first lens of dioptric power +0, and a second lens of dioptric power −2.5. Increasing the strength differences of the lenses in this manner or in similar manners can further improve the focusing abilities of the subject.

It should be noted that prisms may be used in a similar manner. For example, a subject may be provided with an apparatus which includes a prism having a first prism angle. The subject may be asked to look through the prism and to focus on a first indicia, thus testing the vergence ability of the subject. The subject may then be provided with a second apparatus which may include a second prism, for example, having a second prism angle. The subject may then be asked to look through the second prism and focus on the same or a different indicia. In this way a subject's vergence ability may be advantageously measured and/or tested.

It should also be noted that the indicia that the subject may be asked to focus on may be any number of optical or non-optical objects and/or visual indicia, including but not limited to: eye charts, Landolt Cs, pictures, moving or stationary objects, or any indicia or combination of indicia as would be obvious to one of ordinary skill in the art.

The apparatuses in accordance with the present invention may be made of aluminum, plastic, ceramic, rubber, glass, cloth, leather, metal, mesh, or any material or combination of materials. For example, an apparatus may comprise a frame that is made of plastic and lenses that are made of glass. The frame may be covered in certain areas by a soft material, such as rubber or cloth, to provide additional comfort and the appearance of refinement to the subject. For example, a bridge piece may be made of or covered in rubber or a soft plastic, such that it may provide increased comfort if rested against the subject's nose, while the handles may be made of a combination of ridged plastic and rubber to provide a readily grippable surface. Or, in another example, an apparatus may comprise a frame that is made of hardened rubber and prisms. One of ordinary skill in the art will appreciate that a great number of combinations of materials could be utilized in apparatuses in accordance with the present invention.

The invention claimed is:

1. An apparatus for training the visual focusing ability of a subject, the apparatus comprising:
    a partially cylindrical frame, the partially cylindrical frame comprising:
    (i) a partially circumferential surface;
    (ii) a first axial boundary;
    (iii) a first optical element assembly oriented generally along a first plane, the first optical element assembly comprising a first pair of openings to receive optical elements, a first nose notch, and a first edge, the first edge being opposite the first nose notch; and
    (iv) a second optical element assembly oriented generally along the first plane, the second optical element assembly comprising a second pair of openings to receive optical elements, a second nose notch, and a second edge, the second edge being opposite to the second nose notch and being adjacent to the first edge of the first optical element assembly; and
    a first pair of optical elements, the first pair of optical elements having a first optical characteristic;
    a second pair of optical elements, the second pair of optical elements having a second optical characteristic; and
    a handle, the handle being coupled to the partially cylindrical frame and oriented along the first axial boundary of the partially cylindrical frame such that rotating the partially cylindrical frame allows for a reduction in the amount of rotation to visually align to the subject's eyes the first optical element and the second optical element.

2. The apparatus of claim 1 wherein the first nose notch and the second nose notch are composed of a soft material.

3. The apparatus of claim 1 wherein the handle is composed of a soft material.

4. The apparatus of claim 1 wherein the first pair of optical elements comprises a first pair of lenses, wherein the first optical characteristic of the first pair of optical elements comprises a first focal length, wherein the second pair of optical elements comprises a second pair of lenses, and wherein the second optical characteristic of the second pair of optical elements comprises a second focal length.

5. The apparatus of claim 4, wherein the first focal length is approximately equal to the negative of the second focal length.

6. The apparatus of claim 1 wherein the first pair of optical elements comprises a first pair of prisms, wherein the first optical characteristic of the first pair of optical elements comprises a first prism angle difference, wherein the second pair of optical elements comprises a second pair of prisms, and wherein the second optical characteristic of the second pair of optical elements comprises a second prism angle difference.

7. An apparatus for training the visual focusing ability of a subject, the apparatus comprising:
    a partially cylindrical frame, the partially cylindrical frame comprising:
    (i) a partially circumferential surface;
    (ii) a first axial boundary;
    (iii) a first optical element assembly oriented generally along the partially circumferential surface, the first optical element assembly comprising at least a first opening to receive an optical element and a first generally axially oriented edge;
    (iv) a second optical element assembly oriented generally along the partially circumferential surface, the second optical element assembly comprising at least a second opening to receive an optical element and a second generally axial edge, the second generally axial edge being adjacent to the first generally axially oriented edge; and
    a first optical element, the first optical element having a first optical characteristic;
    a second optical element, the second optical element having a second optical characteristic; and
    a handle, the handle being coupled to the partially cylindrical frame and oriented along the first axial boundary of the partially cylindrical frame such that rotating the partially cylindrical frame allows for a reduction in the amount of rotation to visually align to the subject's eyes the first optical element and the second optical element.

8. The apparatus of claim 7 wherein the first optical element comprises a first lens, wherein the first optical characteristic comprises a first focal length, wherein the second optical element comprises a second lens, wherein the second optical characteristic comprises a second focal length, and wherein the first focal length is approximately equal to the negative of the second focal length.

9. The apparatus of claim 7 wherein the first optical element comprises a first prism, wherein the first optical characteristic comprises a first prism angle, wherein the second optical element comprises a second prism, wherein the second optical characteristic comprises a second prism angle, and wherein the first prism angle is not identical to the second prism angle.

10. The apparatus of claim 7 wherein the partially cylindrical frame further comprises a bridge, the bridge generally axially bisecting the partially cylindrical frame along the circumferential surface.

11. The apparatus of claim 10 wherein the bridge is composed of a soft material.

12. The apparatus of claim 7 wherein the first optical element assembly further comprises a third opening to receive an optical element and wherein the second optical element assembly further comprises a fourth opening to receive an optical element.

13. The apparatus of claim 7 wherein the handle is able to axially rotate through a plurality of axial orientations relative to the partially cylindrical frame.

14. The apparatus of claim 13, further comprising an engagement mechanism that provides axial rotation resistance when the handle is axially oriented in at least one of the plurality of axial orientations.

15. An apparatus for training the visual focusing ability of a subject, the apparatus comprising:
   a first optical element having a first optical characteristic, the first optical element being oriented generally along a first plane, the first plane being oriented such that a generally normal projection from the first plane would be generally radial to an axis of rotation and such that the axis of rotation is not contained within the first plane;
   a second optical element, the second optical element having a second optical characteristic, the second optical element being oriented generally along a second plane not parallel to the first plane, the second plane being oriented such that a generally normal projection from the second plane would be generally radial to the axis of rotation and such that the axis of rotation is not contained within the second plane, the first optical element and the second optical element being coupled together and oriented such that the first optical element and the second optical element are adjacent; and
   a handle, the handle being oriented generally along the axis of rotation and being coupled to the first optical element and to the second optical element.

16. The apparatus of claim 15 wherein the first optical element comprises a first lens and wherein the second optical element comprises a second lens.

17. The apparatus of claim 16, wherein the first optical characteristic comprises the focal length of the first lens, wherein the second optical characteristic comprises the focal length of the second lens, and where the focal length of the first lens is approximately equal to the negative of the focal length of the second lens.

18. The apparatus of claim 15 wherein the first optical element comprises a first prism, and wherein the second optical element comprises a second prism.

19. The apparatus of claim 18, wherein the first optical characteristic comprises the prism angle of the first prism, wherein the second optical characteristic comprises the prism angle of the second prism, and wherein the prism angle of the first prism is not identical to the prism angle of the second prism.

20. The apparatus of claim 15, further comprising a third optical element oriented generally along the first plane, and a fourth optical element oriented generally along the second plane.

21. The apparatus of claim 15 wherein the handle is able to axially rotate through a plurality of axial orientations relative to the partially cylindrical frame.

22. The apparatus of claim 21, further comprising an engagement mechanism that provides axial rotation resistance when the handle is axially oriented in at least one of the plurality of axial orientations.

23. A method for training the visual focusing ability of a subject utilizing an optical element apparatus, the method comprising:
   (1) providing a subject with a first optical element apparatus, the first optical element apparatus comprising:
   a partially cylindrical frame, the partially cylindrical frame comprising:
   a partially circumferential surface;
   a first axial boundary;
   (a) a first optical element assembly oriented generally along a first plane, the first optical element assembly comprising a first pair of openings to receive optical elements, a first nose notch, and a first edge, the first edge being opposite the first nose notch; and
   (b) a second optical element assembly being generally along the first plane, the second optical element assembly comprising a second pair of openings to receive optical elements, a second nose notch, and a second edge, the second edge being opposite to the second nose notch and being adjacent to the first edge; and
   (ii) a first pair of optical elements, the first pair of optical elements having a first optical characteristic;
   (iii) a second pair of optical elements, the second pair of optical elements having a second optical characteristic; and
   (iv) a handle, the handle being coupled to the partially cylindrical frame and oriented along the first axial boundary of the partially cylindrical frame such that rotating the partially cylindrical frame allows for a reduction in the amount of rotation to visually align to the subject's eyes the first optical element and the second optical element;
   (2) instructing the subject to hold the first optical element apparatus by the handle;
   (3) instructing the subject to look through the first pair of optical elements and to focus on an indicia;
   (4) instructing the subject to rotate the first optical element apparatus approximately 180 degrees about the handle; and
   (5) instructing the subject to look through the second pair of optical elements and to focus on an indicia.

24. The method of claim 23, further comprising the step of measuring the focusing ability of the subject.

25. The method of claim 23, further comprising the step of displaying an indicia.

26. The method of claim 25, further comprising the step of changing the displayed indicia.

27. The method of claim 23, further comprising iteratively repeating steps (3)-(5).

28. The method of claim 23, further comprising the steps of:
   providing a subject with a second optical element apparatus, the second optical element apparatus comprising:
   (i) a frame, the frame comprising:
   (a) a first optical element assembly oriented generally along a first plane, the first optical element assembly comprising a first pair of openings to receive optical elements, a first nose notch, and a first edge, the first edge being opposite the first nose notch; and
   (b) a second optical element assembly being generally along the first plane, the second optical element assembly comprising a second pair of openings to receive optical elements, a second nose notch, and a second edge, the second edge being opposite to the second nose notch and being adjacent to the first edge; and
   (ii) a first pair of optical elements, the first pair of optical elements having a first optical characteristic;
   (iii) a second pair of optical elements, the second pair of optical elements having a second optical characteristic; and
   (iv) a handle, the handle being oriented generally along a second plane, the second plane not being parallel to the first plane;
   instructing the subject to hold the second optical element apparatus by the handle;

instructing the subject to look through the first pair of optical elements on the second optical element apparatus and to focus on an indicia;

instructing the subject to rotate the second optical element apparatus approximately 180 degrees about the handle; and instructing the subject to look through the second pair of optical elements on the second optical element apparatus and to focus on an indicia.

29. A method for training the visual ability of a subject using a first optical element and a second optical element, the method comprising:

(1) instructing a subject to look through the first optical element and to focus on an indicia, the first optical element having a first optical characteristic, the first optical element being oriented generally along a first plane, the first plane being oriented such that a generally normal projection from the first plane would be generally radial to an axis of rotation and such that the axis of rotation is not contained within the first plane;

(2) instructing the subject to rotate the first optical element and the second optical element around the lateral axis of rotation;

(3) instructing the subject to look through the second optical element and to focus on an indicia, the second optical element having a second optical characteristic, the second optical element being oriented generally along a second plane not parallel to the first plane, the second plane being oriented such that a generally normal projection from the second plane would be generally radial to the axis of rotation and such that the axis of rotation is not contained within the second plane.

30. The method of claim 29, further comprising the step of measuring the visual ability of the subject.

31. The method of claim 29, further comprising the step of displaying an indicia.

32. The method of claim 29, further comprising the step of changing the displayed indicia.

33. The method of claim 29, further comprising iteratively repeating steps (1)-(3).

\* \* \* \* \*